United States Patent [19]

Ackerman

[11] 4,290,891

[45] Sep. 22, 1981

[54] METHOD FOR GROWING A DEAMMONIFYING CULTURE AND USE THEREOF IN WASTEWATER TREATMENT

[76] Inventor: Roy A. Ackerman, P.O. Box 5072, Charlottesville, Va. 22903

[21] Appl. No.: 128,207

[22] Filed: Mar. 7, 1980

Related U.S. Application Data

[62] Division of Ser. No. 891,975, Mar. 30, 1978, Pat. No. 4,218,540.

[51] Int. Cl.³ .............................................. C02F 3/34
[52] U.S. Cl. ................................................. 210/611
[58] Field of Search ................ 210/2, 11, 610, 611, 210/612; 435/262, 822, 832, 874, 885

[56] References Cited

U.S. PATENT DOCUMENTS

| | | | |
|---|---|---|---|
| 3,464,919 | 9/1969 | Barta et al. | 210/11 |
| 3,660,278 | 5/1972 | Mimura et al. | 210/11 |
| 3,801,499 | 4/1974 | Luck | 210/11 |

Primary Examiner—Thomas G. Wyse
Attorney, Agent, or Firm—Pollock, Vande Sande & Priddy

[57] ABSTRACT

A method for growing a culture capable of degrading ammonia which includes inoculating a mediium with a culture identified as ATCC 31381 or one or more of the primary cultures thereof; wherein the medium is a semi-solid containing ground peanut hulls, water, a carbonate source, an ammonia source and a phosphate source. The culture is suitable for treating waste waters to degrade ammonia therein.

6 Claims, 4 Drawing Figures

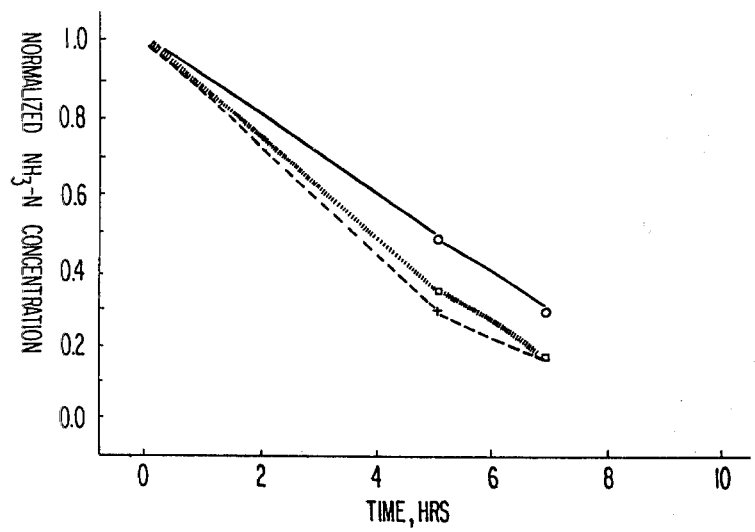
FIG. 1 AMMONIA DEGRADATION EFFECTED BY 1-WEEK-OLD CULTURE ON MEDIA LISTED IN TABLE I, 20C.
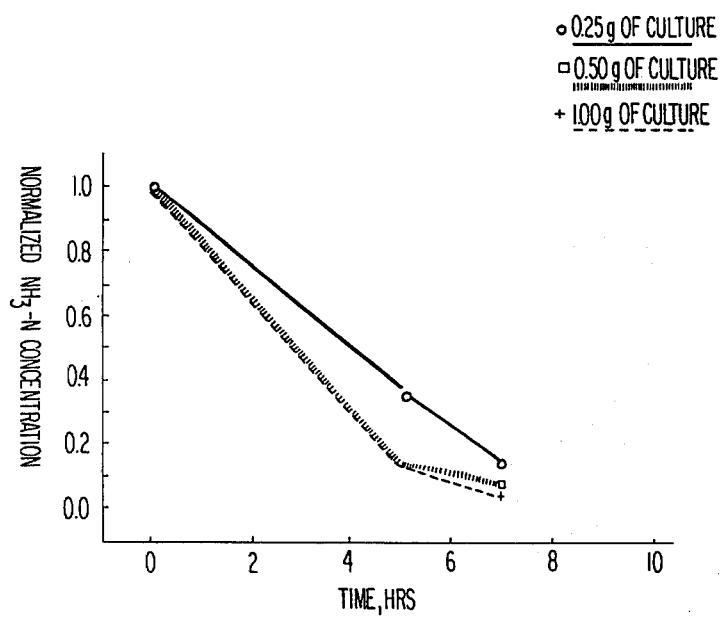
FIG. 2 AMMONIA DEGRADATION EFFECTED BY 1-WEEK-OLD CULTURE ON MEDIA LISTED IN TABLE I, 30C.

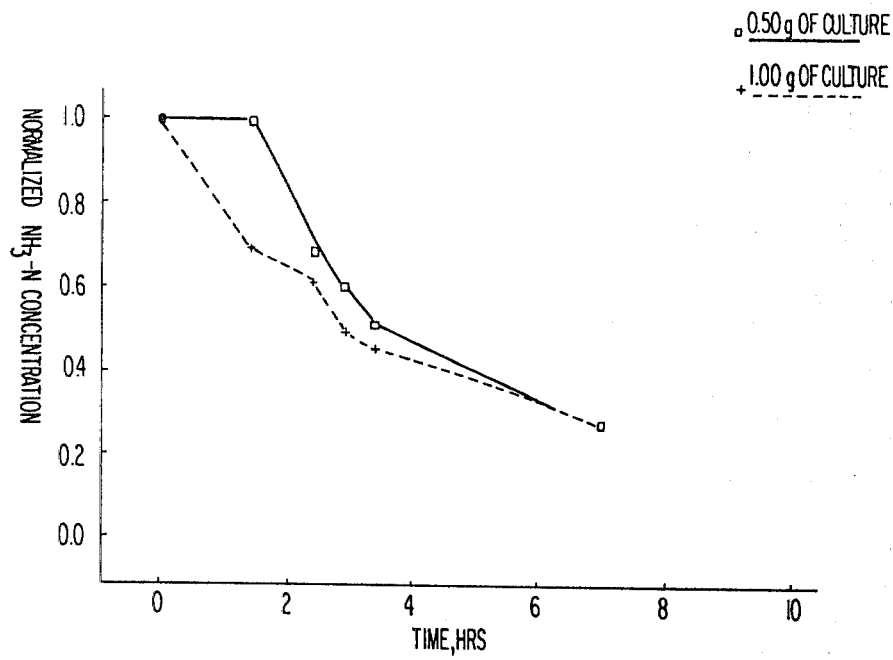
FIG. 3 AMMONIA DEGRADATION EFFECTED BY 6-MONTH-OLD CULTURE ON MEDIA LISTED IN TABLE 1, 20°C.
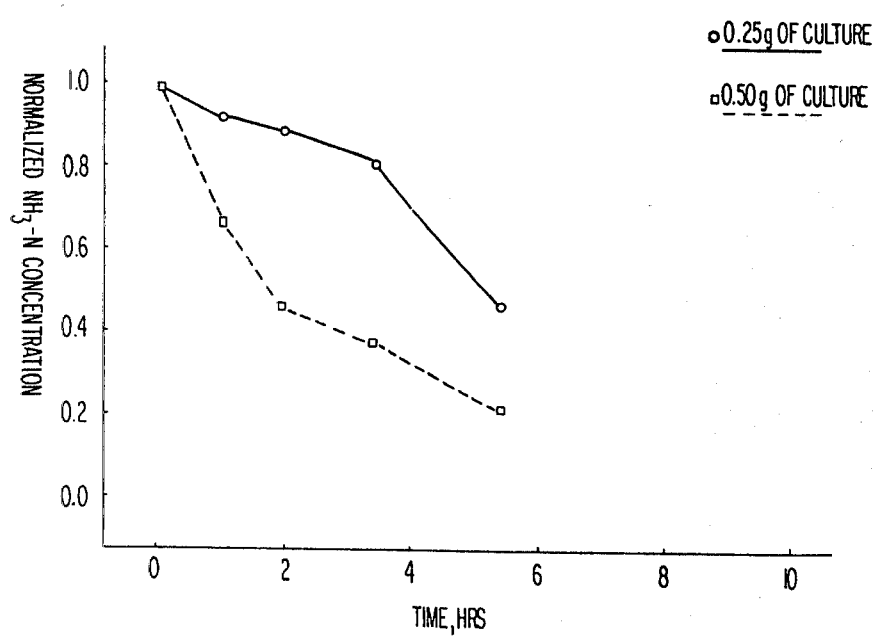
FIG 4 AMMONIA DEGRADATION EFFECTED BY 6-MONTH-OLD CULTURE ON MEDIA LISTED IN TABLE 1, 30°C.

METHOD FOR GROWING A DEAMMONIFYING CULTURE AND USE THEREOF IN WASTEWATER TREATMENT

This is a division of application Ser. No. 891,975, filed Mar. 30, 1978, now U.S. Pat. No. 4,218,540.

CROSS-REFERENCE TO RELATED APPLICATIONS

The present application embodies the inventions disclosed in Invention Disclosure Document No. 065159 completed Oct. 25, 1977, disclosure of which is incorporated herein by reference.

FIELD OF THE INVENTION

The present invention is concerned with growing certain cultures capable of degrading ammonia and particularly the use of a semisolid medium containing peanut hulls. The present invention is also concerned with the use of the cultures in the treatment of waste water.

BACKGROUND OF THE INVENTION

The treatment of waste water has a number of problems associated therewith. In particular, noxious odors in sewage treatment facilities result partially from ammonia gas and the partial anaerobic digestion of proteinaceous wastes. Concomitant with the formation of ammonia is an increase in the pH of the system. Accordingly, organisms sensitive to high pH and/or to ammonia are killed. In addition, after the depletion of oxygen due to the oxidation of ammonia, those organisms capable of producing sulfides grow to a large extent, which in turn causes significant odor problems.

In order to overcome this problem, methods for retrading and when possible for preventing the formation of free ammonia have been suggested. In particular, the bacteria known as Nitrosomonas and Nitrobacter cooperate to convert ammonia to nitrate. However, the presence of nitrate tends to limit the production of additional amounts of nitrate. Moreover, acid is formed during oxidation of the ammonia. In many systems, denitrifying bacteria are also required to convert the nitrate to nitrogen gas (since there are health limits for nitrate levels in water).

Therefore, an object of the present invention is to provide microorganisms, which convert ammonia to nitrogenous gases, without the production of significant amounts of nitrate. This could eliminate the necessity for additional bacteria to effect denitrification.

It is further recognized that many of the bacteria employed in wastewater treatment die quickly when left dormant in dilute suspension or form spores that require time to germanate before becoming metabolically functional. Therefore, a further object of the present invention is to provide a microorganism which can be stored over relatively long periods of time (several months) without significantly losing its deammonifying capabilities.

Moreover, various bacteria capable of metabolizing ammonia are not effective in the presence of carbonaceous substrates. In such case, two separate chambers are required for treatment; the first of which is to treat the carbonaceous substrates, followed by oxidizing the ammonia. The microorganisms of the present invention can act in the presence of carbonaceous substrates. Accordingly, a waste treatment system employing the microorganisms of this invention makes it possible to employ only one instead of multiple chambers in a waste-treatment system.

The process of preparing the microorganisms utilizes a solid medium which provides for a number of desirable advantages including easy storage, transportation and utilization to full advantage. Also, since the microorganisms are present on a solid medium, seeding of the waste-systems is convenient, which, in turn, reduces the time between start-up and steady state. Moreover, the culture can be readily added in a continuous manner.

SUMMARY OF INVENTION

The present invention is concerned with growing a culture of the microorganisms identified as ATCC 31381 or one or more of the primary cultures thereof, which culture is capable of converting ammonia to other nitrogenous products. The process includes obtaining a semisolid medium of ground peanut hulls, water, a carbonate source, an ammonia source and a phosphate source. The medium can also contain up to about 12% by weight based upon the weight of the peanut hulls of a cereal grain. The medium is inoculated with a culture of the microorganisms identified as ATCC 31381 or one or more of the primary cultures thereof.

The present invention is also concerned with the use of a culture of the microorganism identified as ATCC 31381 or one of the primary cultures thereof to treat waste water to degrade ammonia therein. The wastewater treatment with the microorganisms should be conducted under aerobic conditions.

BRIEF DESCRIPTION OF THE DRAWINGS

FIGS. 1 and 2 are graphs illustrating ammonia degradation of a one-week old culture at 20° C. and 30° C., respectively.

FIGS. 3 and 4 are graphs illustrating ammonia degradation of a six-month old culture at 20° C. and 30° C., respectively.

DESCRIPTION OF PREFERRED EMBODIMENTS

The medium suitable for growing the microorganisms is a semisolid medium containing peanut hulls, water, a carbonate source, an ammonia source, and a phosphate source. The carbonate source is employed in amounts sufficient to provide the medium with a pH in the range from about 5 to 9. The ammonia source is present in amounts sufficient to assure that the ammonia is not depleted during the process. The peanut hulls are present in amounts sufficient to provide adequate sites for growth of the microorganism. The water is added to provide a semisolid medium to facilitate mixing and contact of the culture and nutrients with the peanut hulls. The amount of water is usually present in an amount to provide a water-substrate ratio within the range of about 1.3:1 to about 0.7:1.

In addition, if desired, the medium can optionally contain a magnesium source, a chloride source and trace amounts of such metals as iron, zinc, copper, molybdenum, cobalt, and manganese. It is recognized that these additional materials are not always (or may not be) necessary. The medium can also contain about 12% by weight based upon the weight of the peanut hulls of a cereal grain such as wheat bran, rice bran, oat hulls, soybean hulls and the like. For a discussion of nutrients, attention is directed to M. S. Finstein et al, [*Water Research*, 6; pp. 31–40 (1972)].

Also, it is preferred that growth of the culture be initially conducted in a solution of the desired nutrients to develop a suitable mass of microorganisms to be added to the peanut hull substrate. By using this two-stage preparation, mixing the various components is easier since the nutrients and culture are in a liquid form. Also, this procedure helps assure adequate contact of the culture with the substrate. The use of two steps also makes it possible to reduce the time used to grow the microorganism. Growth in the liquid medium is generally carried out for about 1 to 5 days until a satisfactory biomass is obtained, which can be observed by the formation of small brown pin-like flocs.

The microorganism(s) employed can be that identified as ATCC 31381 and/or one or more of the primary cultures thereof. The primary cultures can be obtained from the microorganisms identified as ATCC 31381 by standard separatory procedures for bacterial isolation. For instance, see Isolation of Pure Cultures by Plating Methods [*The Microbial World*—R. Y. Stanier et al, Prentice Hall, N.J. (1970)]. It is believed that the primary cultures include Enterobacter agglomerans, a group D Streptococcus, at least one and possibly two Bacilli, and at least one and possibly two Pseudomonads. The primary cultures have been isolated with Hektoen's agar plates and with Finstein's media.

The microorganisms are grown under aerobic conditions. The microorganisms identified as ATCC 31381 are on deposit at The American Type Culture Collection, 12301 Parklawn Drive, Rockville, Md. Access to the culture will be available during pendency of this patent application to anyone determined by the Commissioner of Patents to be entitled thereto under 37 CFR 1.14 and 35 USC 122. All restrictions by applicant on the availability to the public of the culture so deposited will be irrevocably removed upon the granting of the patent. The culture is now available to the public and the culture will be permanently available to the public through a depository, affording permanence of the deposit and ready accessibility thereto by the public, if the patent is granted.

The microorganisms described hereinabove are useful in the treatment of waste waters to destroy ammonia therein. Examples of some systems which can be treated in accordance with the present invention include sewage treatment facilities, lagoons, septic systems, aquariums, and waste holding tanks such as those used in airplanes, campers, recreational vehicles, and boats. The microbial product as produced above is added to the waste water in amount sufficient to destroy the desired amount of ammonia present and will vary greatly depending upon the concentration of ammonia in the waste being treated. Generally the product is employed in amounts ranging from about 0.5 to about 6 pounds per million gallons of waste per day. The wastewater is generally maintained at temperatures ranging from about 0° to 40° C. during the treatment.

The following examples are presented to further illustrate the present invention:

EXAMPLE 1 (Growth of Microorganisms)

About 1 gram of microorganisms identified as ATCC 31381 is added to the medium described hereinbelow in Table 1. Aeration (either mechanical aeration or shaker culture) is then supplied for one (1) to five (5) days, until a satisfactory biomass is developed (light brown pin-like flocks are usually observed).

The semisolid culture medium described hereinbelow in Table 2 is then inoculated with the inoculum culture produced above. Generally about 1 to 30 liters of the inoculum are used. It is understood that microorganisms of the type ATCC 31381 need not be added initially to the medium described in Table 1 but can be added directly to the semisolid culture medium.

TABLE 1

| Culture medium employed for shake-flask test | | |
|---|---|---|
| $CaCO_3$ | 10.0 | g |
| $(NH_4)_2SO_4$ | 1.5 | g |
| $K_2HPO_4$ | 0.5 | g |
| $MgSO_4$ | 50 | mg |
| $CaCl_2 \cdot 2H_2O$ | 20 | mg |
| $KHCO_3$ | 30 | mg |
| tmm[a] | 1 | ml |
| tap water | 1 | liter |

TABLE 2

| Semisolid medium composition used to produce final product culture | | |
|---|---|---|
| Ground peanut hulls | 15.0 | kg |
| $CaCO_3$ | 454 | g |
| $(NH_4)_2SO_4$ | 100 | g |
| $K_2HPO_4$ | 10 | g |
| $MgSO_4$ | 1.0 | g |
| $CaCl_2 \cdot 2H_2O$ | 0.5 | g |
| $KHCO_3$ | 0.75 | g |
| Tap water | 7 | liters |
| tmm[a] | 25 | ml |

[a] The trace metal mixture was of the following composition (g/liter): $FeSO_4 \cdot 7H_2O$, 0.028; $ZnSO_4 \cdot 7H_2O$, 0.140; $CuSO_4 \cdot 5H_2O$, 0.025; $NaMoO_4 \cdot 2H_2O$, 0.024; $CoCL_2 \cdot 6H_2O$, 0.024; $MnSO_4 \cdot H_2O$, 0.084.

The medium was prepared by thoroughly mixing the water and the ground peanut hulls in a Hobart mixer, and then it was autoclaved. The substrate was cooled to about 25° C. after which it was inoculated with about 1.5 liters of the nitrifying inoculum produced above. This substrate with about 55–60 wt% moisture was placed in layers 2.5 cm thick on sterilized, perforated, stainless-steel trays. After a five-day incubation period at 24° C. and a minimum of 90% humidity, the incubator was reduced to 20% humidity. The material was then allowed to dry for 2 days to approximately 10% moisture to provide the desired product.

As discussed hereinabove, the primary cultures have been isolated on Hektoen's Agar Plates and on Finstein's media. If desired, these cultures can be used as inoculum sources. One loop of each culture is transferred to a vessel containing a small portion of sterile medium identified in Table 1. Aeration is then effected. Each day additional sterile medium is added until the desired volume has been added. The culture is then allowed to develop for an additional one (1) or two (2) days. This then serves as the nitrogen-metabolizing inoculum to the semisolid system described above.

Moreover, if desired, any number of the primary cultures can be mixed with each other and/or with the culture identified as to provide desired relative amounts of any number of these primary cultures. This makes it possible to tailor-make a microbial product for a specific purpose or problem.

The original material from which the microorganisms ATCC 31381 was produced involved removing 100 ml of fluid from the aerobic chamber from two of applicant's waste treatment test units. These samples were mixed together and grown using the medium described in Table 1. Five milliliters of the fluid mixture from the unit served as the inoculum for each of 12 1-liter flasks which contained 250 ml of sterile medium. The temperature was maintained at 28°±1° C. After 1 wk., the ammonia levels in the flasks were determined. Of these flasks, eight had converted ≧50% of the initial ammonia to nitrate. These eight flasks then served as inoculum for the second selection phase in the medium described in Table 1. This time all 12 flasks provided ≧80% ammonia converstion.

These cultures were then grown on the semisolid substrate identified in Table 2.

EXAMPLE 2

A one-week old semisolid culture was tested for its ammonia conversion in shake flasks employing the medium described hereinabove in Table 1. The results obtained for 20° C. at the various concentrations after 7 hours incubation are illustrated in FIG. 1. The results obtained for 30° C. at the various concentrations after 7 hours incubation after storage for 6 months at uncontrolled temperatures ranging from −20° C. to 30° C. was tested for its ammonia conversion in shake flasks employing the medium described hereinabove in Table 1. The results obtained at various concentrations after 7 hours incubation for 20° C. and 30° C. are illustrated in FIGS. 3 and 4. As illustrated in FIGS. 1-4, the ammonia conversions were basically first order with respect to time, until they reached an asymptotic level. The slope increased with increasing inoculum size. The increased inoculum size, in addition to increasing the slope, decreased the lag in conversion. The effect of higher temperature was to increase the conversion rate, as expected; the ultimate degree of conversion was basically the same, however. This phenomenon is expected if the maximum population density were the same for all inoculum levels. The major effect of storage was only 10-15% decrease in the ultimate conversion at 7 hours incubation.

EXAMPLE 3

One-week old semisolid culture prepared by the above method was added to two waste-treatment systems which treat and recycle all of the water (e.g., zero discharge units). One of the systems had just started up (about 10 days) and the other had operated at 2.1 g/liter of ammonia-nitrogen ($NH_3$—N) for 60 days and was considered sour.

These systems were dual-function, with mixed cultures (i.e., they affected nitrogenous and carbonaceous degradation simultaneously). The start-up-unit, operating at a 3-h hydraulic retention time, had influent levels of 1.84 g/liter inorganic carbon and 0.92 g/liter $NH_3$—N. After 18 days, pseudo-steady state for ammonia was attained (8 days post-culture addition). The levels in the fermentor were basically (±10%) 1.22 g/liter organic carbon and 0.12 g/liter $NH_3$—N. The "sour" unit, operating at a 6 h HRT, had influent levels of 5 g/liter organic carbon and 2.5 g/liter $NH_3$—N. Prior to seeding, this system had substrate levels of 10.2 and 2.1 g/liter, respectively. Ten days after seeding, the organic carbon level was 10.2 g per liter and the $NH_3$—N concentration was 0.44 g/liter.

In both systems, about an 85% ammonia conversion was obtained. There seemed to be no effect of hydraulic retention time upon the efficiency of ammonia conversion. Moreover, the systems of the present invention are capable of deammonification at high rates, even in the presence of carbonaceous substrates. Olenik [*Nitrification Effects in Waste Process*, PhD thesis. Rutgers University, New Brunswick, N.J. (1974)] found somewhat similar occurrences in his study of nitrification in sewage systems. However, the lack of nitrates was attributed to a heterotrophic carbonaceous strain which utilized ammonia as substrate. The cultures employed in the present invention produced nitrates from a single ammonia substrate and not from a fixed substrate, but did not have any appreciable activity when a "pure" carbonaceous medium was supplied.

Although nitrates were produced from ammonia in the batch shake flasks, in continuous systems, there was only a minimal production of nitrates. Less than 50 mg/liter of $NO_3$—N were observed in any of the recycle systems. Also, dissolved oxygen tensions were continuously tested and it was observed that they never fell below 2 mg/liter. Had the dissolved oxygen fallen below that level (2 mg/liter), dissimilatory nitrate reduction could have been effected, even with increased oxygen levels later on. Such an occurrence would eliminate the possibility of observing high $NO_3$—N levels [Krul, J. M., The relationship between dissimilatory nitrate reduction and oxygen uptake by cells of an Alcaligenes strain in flocs and in suspension and by activated sludge flocs, *Water Res.* 10: 337–341 (1976)]. Since the dissolved oxygen ranged from 3 to 7 in the waste recycle units, it is postulated that an alternate electron pathway exists. Such a pathway was found to occur for hydrogen production and nitrogen fixation processes [Mitsui, Long range concepts: Applications of photosynthetic hydrogen production and nitrogen fixation research. Capturing the Sun through Bioconversion (conference), Washington, D.C. (1976)].

This pathway was hypothesized since no increase in the volatile suspended solids was noted after the addition of our semisolid culture. The possibility that ammonia was utilized for metabolism is therefore discounted, since bacterial density should increase if ammonia were metabolized. Work currently is being performed to ascertain the fate of nitrogen in these mixed substrate systems.

Cultures employed according to the present invention are available under the trade designation AT5N.

Semisolid substrate is meant to refer to said substrate which is moist. During culture production, it usually contains amounts of water in the ranges discussed hereinabove, and after such production it is dried to contain less than 25% moisture.

The culture is preferably employed in combination wth the substrate on which it is prepared, or if desired can be employed in liquid form in a medium suitable for its production (e.g., one that contains a carbonate source, an ammonium source, and a phosphate source in water). When employing it in a liquid form, preferably about 0.5 to 25 gallons per million gallons of wastewater treated are used. The amounts when present in the substrate are preferably about 0.5 to 6 pounds per million gallons of wastewater treated.

What is claimed is:

1. A method for treating waste water and for degrading ammonia in said waste water which comprises:
   a. obtaining a culture having the identification of ATCC 31381 or one of its primary cultures, or mixtures thereof;

b. adding said culture to said waste water in an amount sufficient to degrade a predetermined quantity of said ammonia;

c. said culture and waste water being under aerobic conditions.

2. The method of claim 1 wherein about 0.5 to about 6 pounds per million gallons of water per day of said culture on peanut hulls is employed.

3. The method of claim 1 wherein said waste is at a temperature of about 0° to 40° C. during the treatment.

4. The method of claim 1 wherein said primary culture is selected from the group of Enterobacter agglomerans, Group D Streptococcus, Bacilli, Pseudomonad, or mixtures thereof.

5. The method of claim 1 which comprises obtaining a culture having the identification ATCC 31381.

6. The method of claim 1 which further degrades carbonaceous substances.

* * * * *